United States Patent [19]

Holtkamp, Sr.

[11] Plant 4,375

[45] Feb. 6, 1979

[54] ANTHURIUM PLANT

[76] Inventor: Hermann Holtkamp, Sr., Kueningsmuehle, 2 Dingden, 4236 Hamminkeln, Fed. Rep. of Germany

[21] Appl. No.: 920,225

[22] Filed: Jun. 28, 1978

[51] Int. Cl.[2] ..... A01H 5/00

[52] U.S. Cl. ..... Plt./88

[58] Field of Search ..... Plt./88

*Primary Examiner*—Robert E. Bagwill
*Assistant Examiner*—James R. Feyrer
*Attorney, Agent, or Firm*—Donald D. Jeffery

[57] ABSTRACT

The new anthurium cultivar Senior II is characterized by its fiery red, generally heart-shaped spathe which have a wavy surface and a slight indentation along an edge thereof. Straight and wiry petioles position the spathe slightly above the leaves, which are medium to dark green. The new cultivar has an early blooming habit, a slightly spreading growth habit, and can be asexually reproduced only by tissue culture.

1 Drawing Figure

1

The present invention comprises a new and distinct cultivar of anthurium, botanically known as *Anthurium andraeanum,* and hereinafter referred to by the cultivar name Senior II.

The new cultivar is a product of a planned breeding program, and was originated from a cross made during such a program in Isselburg, Rhineland, Germany. The female, or seed parent was GUATMALA 83, and the male, or pollen parent was GUATMALA 45. Senior II was discovered and selected as a flowering plant within the progeny of the stated cross by me in a controlled environment in Isselburg, Rhineland, Germany, and subsequent asexual reproduction has demonstrated that the combination of characteristics as herein disclosed for the new cultivar are firmly fixed and are retained through successive generations of asexual reproduction. From experiences to date, asexual reproduction of the new cultivar is only possible by means of tissue culture.

The following traits have been repeatedly observed and in combination distinguish Senior II as a new and distinct cultivar:

1. The spathe or blossoms are fiery red and of medium size, being approximately 85–200 mm. in diameter.
2. The shape of the spathe is generally heart-shaped, with one rim or edge thereof being slightly indented.
3. The petioles are straight and strong, and the spathe stand slightly above the leaves.
4. The leaves are relatively large, and medium to dark green in color, with the underside of the leaves being somewhat lighter, and the leaves in young plants being generally brownish.
5. The new cultivar is loose or slightly spreading in growth habit, being 40–45 cm. in height when grown to maturity in a 12 cm. pot.
6. The spadix is approximately 40–50 mm. long, 8–9 mm. in diameter, having a generally yellow color at early growth stages and maturing into a generally ivory white color at maturity.
7. When compared to other commercially available anthuriums of this species, Senior II blooms relatively early, after 10–12 months of cultivation in a 12 cm. pot. The spathe when first blooming are generally medium sized and become larger as the plant matures in growth.

The accompanying photographic drawing shows a typical specimen of the new cultivar, with the colors appearing in the photograph being as true as possible with color illustrations of this type.

2

The following observations, measurements and values describe plants grown in Isselburg, Rhineland, Germany, under greenhouse conditions which closely approximate those generally used in horticultural practice. Color references are made to the Royal Horticultural Society (RHS) Color Chart, 1966 edition, except where general color terms of ordinary significance are used.

Botanical classification: *Anthurium andraeanum,* cultivar name, Senior II.

Parentage:

*Male parent.*—*Anthurium andraeanum* GUATMALA 45.

*Female parent.*—*Anthurium andraeanum* GUATMALA 83.

Propagation: At the present time, the new cultivar holds its distinguishing characteristics from generation to generation only by asexual reproduction by tissue culture.

Plant: When grown in a 12 cm. pot, the plant is from 35–40 cm. tall and approximately 35 cm. in diameter.

Leaves:

*Form and size.*—The leaves are generally heart shaped, with a distinct point; the diameter, depending on the size of the plant, is 120–180 mm., and occasionally larger. The leaves of each plant, when fully grown, are of equal size and shape, and individual leaves are slightly indented at one location along the edge.

*Texture.*—Leathery and very smooth, slightly shiny.

*Veins.*—Very visible and well-developed, particularly standing out on the underside of the leaves.

*Color.*—Mature, upperside, 137 A; young leaves 152 A. On the underside, the color is 139 C. The petiole is very straight and wiry.

Flowers:

*Buds.*—The spathe is rolled around the spadix, is shaped and pointed like a cigar; after opening, the spathe stands slightly above the leaves. The bud stands horizontally on the pedicle, and the open blossom stands slightly bent forward.

Spathe (blossom):

*Size.*—Approximately 80 × 150 mm.

*Color.*—Upperside, 45 A-B. Underside, 46 B-C.

*Arrangement.*—The spathe stand on straight, wirey pedicles, and are slightly bent forward at an angle of approximately 45° to the pedicle.

*Shape.*—At full bloom, the spathe is of a roundish heart shape. The veins are very visible, irregular, and grooved on the upperside and underside. The edge of the spathe often is indented on one side.

*Flowering time.*—After 9–12 months of being potted in a 12 cm. pot, the plant will be in bloom with 2–4 blossoms and buds. Small blossoms are seen earlier.

Reproductive organs: The spadix is approximately 35–45 mm. long and 8–10 mm. in diameter. At an early stage, when the pistil and stamens are not yet mature, the spadix is yellow, later becoming white.

*Stamens.*—Around the pistil are four stamens. They are visible only when separating the individual reproductive organs from the pulpy main axle. The stamens are covered with 2 small triangular and 2 square shaped tops; at the center, the stamen is firmly enclosed.

*Anthers and filaments.*—Not clearly visible.

*Pollen.*—white-yellow in color.

*Pistils.*—Firmly grown together with the pulpy main axle and sitting between the stamens. The style is yellow-white and shaped slightly square, approximately 3–5 mm. long.

Roots: Very pulpy and light yellow-brown; tip of roots white, well-branched out. When exposed to light, the roots become light-green.

Disease Resistance: Through experiences to date, very good against traditional diseases.

General observations: Senior II is a very fast growing anthurium which is loose or slightly spreading in growth habit. At an early stage of growth, the plant blooms with medium sized spathe which become bigger with the growth of the plant. The new cultivar is suited both as a potting plant as well as a cut flower. Senior II due to its unique combination of characteristics provides a valuable new cultivar of *Anthurium andraeanum.*

I claim:

1. A new and distinct cultivar of anthurium substantially as described and illustrated, known by the cultivar name Senior II and characterized by the combined features of fiery red, generally heart-shaped spathe having a wavy surface and a slight indentation along an edge thereof; straight and wiry petioles which position the spathe slightly above the leaves; medium to dark green leaves; early blooming habit; slightly spreading growth habit, and by the ability to be asexually reproduced only by tissue culture.

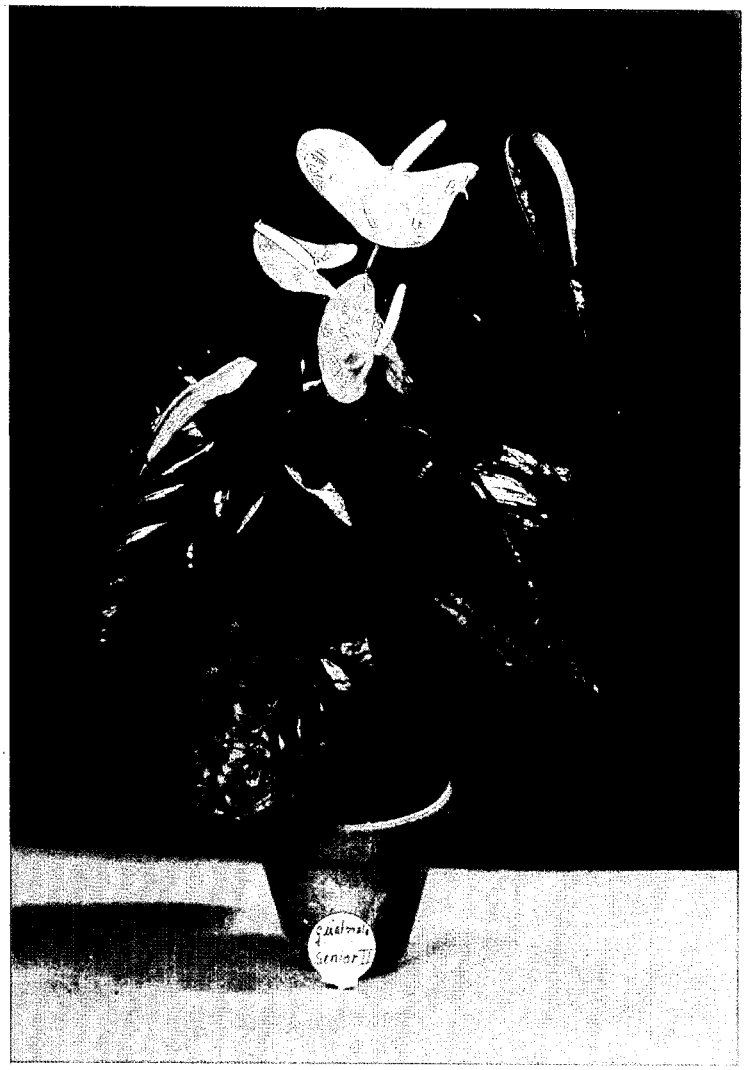

* * * * *